United States Patent [19]

Grier et al.

[11] 4,145,426
[45] Mar. 20, 1979

[54] ANTI-MICROBIAL PIPERIDINO BUTAN-2-ONES

[75] Inventors: Nathaniel Grier, Englewood; Richard A. Dybas, Somerville; Bruce E. Witzel, Westfield, all of N.J.

[73] Assignee: Merck & Co., Inc., Rahway, N.J.

[21] Appl. No.: 816,613

[22] Filed: Jul. 18, 1977

[51] Int. Cl.$^2$ ............... A61K 31/445; C07D 211/44; C07D 211/32; C07D 211/22
[52] U.S. Cl. ...................... 424/267; 546/184; 546/186; 546/187; 546/188; 546/189; 546/190; 546/191; 546/192; 546/208; 546/220; 546/221; 546/225; 546/228; 546/227; 546/235; 546/237; 546/242; 546/245; 546/248; 260/584 A; 106/15 R
[58] Field of Search .............. 260/293.63, 293.71, 260/293.76, 293.78, 293.86, 293.87; 424/267

[56] References Cited
PUBLICATIONS
Barrett, P. A. et al., *J. Chem. Soc.*, 338–349 (1958).

*Primary Examiner*—Natalie Trousof
*Assistant Examiner*—Richard A. Schwartz
*Attorney, Agent, or Firm*—Edmunde D. Riedl; Julian S. Levitt

[57] ABSTRACT

Compounds of the structure:

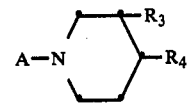

where A is either

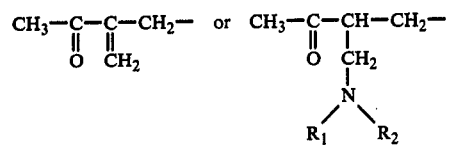

where $R_1$ to $R_4$ are various substituents are active as antibacterials and antifungals.

4 Claims, No Drawings

ANTI-MICROBIAL PIPERIDINO BUTAN-2-ONES

DISCLOSURE OF THE INVENTION

This invention relates to a process for protecting materials of various kinds against infection and damage by microorganisms, as by bacteria and fungi, and to antimicrobial compositions for use in such process.

We have discovered compounds of the following formulas:

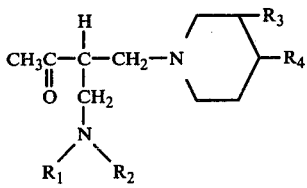

I.

and

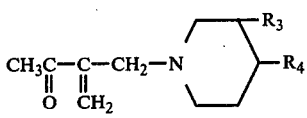

II.

$R_1$ and $R_2$ are independently hydrogen, $C_1$ to $C_8$ alkyl, $C_1$ to $C_8$ hydroxyalkyl, $C_4$ to $C_8$ cycloalkyl, or $R_1$ and $R_2$ taken together form part of a six-membered saturated heterocyclic ring and $R_1$ and $R_2$ are tetramethylene, or pentamethylene, and tetramethylene or pentamethylene substituted at the 3- and 4-position with $R_3$ and $R_4$.

$R_3$ and $R_4$ are hydrogen, $C_1$ to $C_3$ alkyl, hydroxy, $C_1$ to $C_3$ hydroxyalkyl, phenyl, carboxy, carboxamido, N-loweralkylcarboxamido said alkyl having up to four carbons, loweralkoxycarbonyl said alkoxy having up to four carbons, 1-pyrrolidinyl, 1-piperidinyl, provided $R_3$ and $R_4$ are not simultaneously hydrogen.

These compounds possess highly useful antimicrobial activity, are relatively free of objectionable odors, high toxicity hazards and undesirable volatility and can accordingly be employed to protect industrial products and systems of wide variety against the deteriorating action of bacteria and fungi.

In the above formulas the alkyl groups may also be unsaturated (alkenyls), the cycloalkyl groups include cyclopentyl, cyclohexyl and cycloheptyl and the heterocyclic ring may be five or six-membered.

All of the compounds of this invention to our knowledge have heretofore been unknown; however, compounds of Type I in which $R_3$ and $R_4$ are both hydrogen and $R_1$ and $R_2$ together comprise an unsubstituted cycloaliphatic moiety, have been disclosed, e.g. 1,1-bis(-piperidinomethyl)propan-2-one by P. A. Barrett and K. A. Chambers [J. Chem. Soc., 343 (1958)]. The disadvantages associated with the unsubstituted ring compound have been noted.

The I-type compounds of this invention can be synthesized by techniques involving the condensation of 3- and/or 4-substituted piperidines, formaldehyde and acetone:

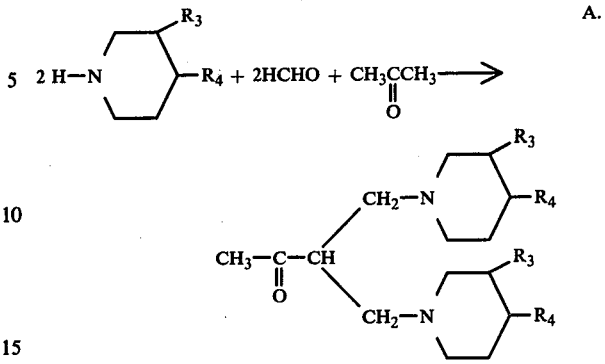

A.

The olefinic elimination products, Type II, may be obtained from the compounds synthesized by A. procedures using a variety of methods such as with heat, salt formation with oxalic acid, by steam distillation to cite some:

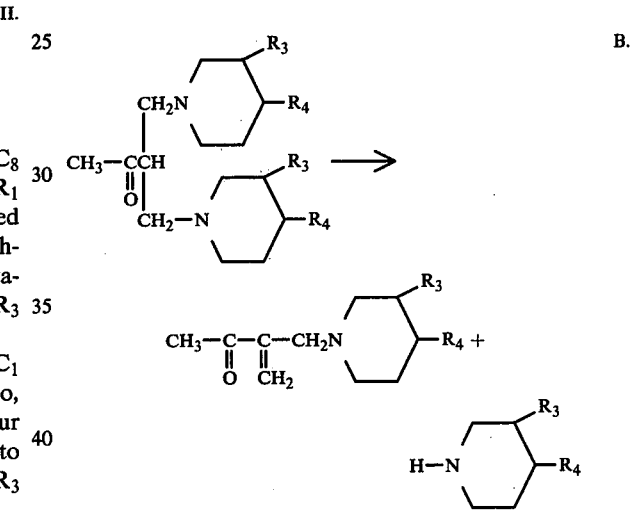

B.

Several routes are suitable for the synthesis of Type I compounds wherein the two base substituents are different. The mono-Mannich base may be prepared:

$$H-N\underset{}{\overset{R_3}{\diagup}}\hspace{-2pt}\underset{}{\diagdown}R_4 + HCHO + CH_3COCH_3 \longrightarrow$$

$$CH_3COCH_2CH_2-N\underset{}{\overset{R^3}{\diagup}}\hspace{-2pt}\underset{}{\diagdown}R_4$$

and reacted with a second mole of formaldehyde and secondary amine:

$$CH_3COCH_2CH_2-N\underset{}{\overset{R_3}{\diagup}}\hspace{-2pt}\underset{}{\diagdown}R_4 + HCHO +$$

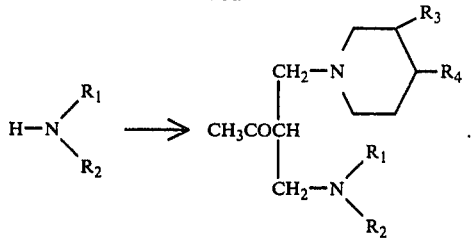

A mole of amine may be added to the olefin II:

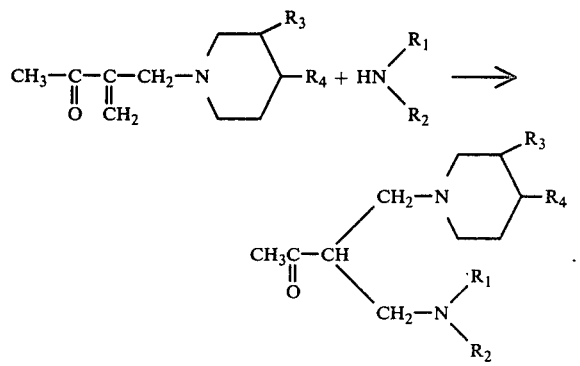

Or, the various sequences outlined may employ the secondary amine,

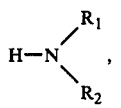

initially to produce the bis-Mannich derivative. Elimination of one mole of amine then provides III

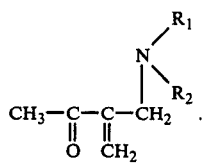

Addition of one mole of

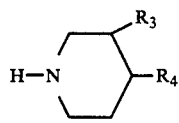

forms Type I compounds.

The compounds are prepared, for Type I products which contain identical substituted piperidine groups by reacting substantially molar ratios of 2:1:2 with respect to amine, acetone and formaldehyde. A considerable excess of the first and/or third reaction component may be used.

A variety of solvents may be used for the synthesis including water, alcohols, ethers as well as an excess of one of the reagents other than acetone. The amines can be used in the Mannich reaction as free bases or in the form of salts such as the acetate or hydrochloride. Generally, elevated temperatures are required in the range of 45° to 110° C. and reaction periods of from 1 to 24 hours. Isolation of products may be accomplished by crystallization or distillation. Any other chemical groupings present in the organic bases employed for the Mannich reaction which contain active hydrogen should preferably be blocked and afterwards liberated by techniques well known in the art.

The addition reactions of Type II olefinic compounds with amines to provide Type I derivatives may be run with a 1:1 molar ratio of reactants in solvents such as water, alcohols, dioxane or mixtures of these or neat. Generally, no heat is required and reaction times may range from ½ to 10 hours. The course of the reaction is readily monitored by measuring the disappearance of the alpha beta unsaturated ketonic moiety as with ultra-violet or infra-red spectral analysis.

Both Type I and Type II compounds can be used in the form of salts derived from inorganic or organic acids. Also, the basic nitrogen-containing groups can be quaternized with such agents as lower alkyl halides, such as methyl, ethyl, propyl, and butyl chloride, bromides and iodides, dialkyl sulfates like dimethyl, diethyl, dibutyl and dilanyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The effectiveness of these compounds as preservatives for aqueous systems is exemplified by the performance in latex paints. Acrylic and polyvinyl acetate coatings were dosed with 0.01% by weight or compounds of this invention and then challenged with a heavy inoculum of *Pseudomonas aeruginosa.* Within 24 hr. all growth was suppressed. After seven days a re-inoculation was made and again there resulted complete inhibition within 24 hr. Control paints which lacked a preservative in the same tests were degraded by the microorganisms. The compounds are effective against gram positive and gram negative bacteria and fungi in such diverse systems as cooling tower water systems, paper mill white water, in brines for enhanced oil recovery, in cutting oil emulsions, resin emulsions, aqueous adhesives and the like. Concentrations of from 0.001% up to 0.5% may be employed depending upon the system and degree of microbial contamination. They may be added neat as powders or liquids, in solution or as dispersions and emulsions in aqueous or non-aqueous media or admixed with inert solid carriers. Adjuvants such as surfactants, spreading agents, defoamers, other antimicrobials, dyes, antifreeze ingredients, film coalescents and the like may be used.

EXAMPLE 1

3-[(4-Hydroxypiperidino)methyl]-4-(hydroxypiperidino)-butan-2-one

A solution of 4-hydroxypiperidine (20.5 g.) in 40 ml. of water is chilled in an ice bath and mixed with acetone (30 ml.) and potassium chloride (15.1 g.). After complete solution there is added dropwise over a 15-minute period formaldehyde, aqueous 35% (18 ml.). The reaction mixture was then stirred 12 hr. at 20°–25° C. It was made alkaline with 50% sodium hydroxide aqueous solution and the resultant two phases separated. The aqueous layer was cooled and extracted several times with methylene chloride. The combined organic phase and methylene chloride extracts were washed with saturated sodium chloride solution and then dried over anhydrous sodium sulfate. After filtration the solvent was stripped under reduced pressure leaving an oil, 24.2 g. Its mass spectrum showed a molecular ion of 183, the infra red and nuclear magnetic resonance proton spectra were in agreement for the product.

In place of 4-hydroxypiperidine the following substituted piperidines may be reacted using the above procedure with formaldehyde and acetone to provide the indicated products.

| | Piperidine Substituent | Product |
|---|---|---|
| 1. | 3-Hydroxy | 3-[(3-Hydroxypiperidino)methyl]-4-(3-hydroxypiperidino)butan-2-one |
| 2. | 3-Hydroxymethyl | 3-[(3-Hydroxymethylpiperidino)methyl]-4-(3-hydroxymethylpiperidino)butan-2-one |
| 3. | 4-Carboxy | 3-[(4-Carboxypiperidino)methyl]-4-(4-carboxypiperidino)-butan-2-one |
| 4. | 3-Carbamyl | 3-[(3-Carbamylpiperidino)methyl]-4-(3-carbamylpiperidino)-butan-2-one |
| 5. | 4-(N-Methylcarbamyl) | 3-{[4-(N-Methylcarbamyl)piperidino]methyl}-4-[4-(N-methylcarbamylpiperidino)]butan-2-one |
| 6. | 4-Ethoxycarbonyl | 3-[(4-Ethoxycarbonylpiperidino)methyl]-4-(3-ethoxypiperidino)butan-2-one |
| 7. | 4-Isopropyl | 3-[(4-Isopropylpiperidino)methyl]-4-(4-isopropylpiperidino)butan-2-one |
| 8. | 3-Methyl-4-hydroxymethyl | 3-[(3-Methyl-4-hydroxymethylpiperidino)methyl]-4-(3-methyl-4-hydroxymethylpiperidino)butan-2-one |
| 9. | 4-Phenyl-4-hydroxy | 3-[(4-Phenyl-4-hydroxypiperidino)methyl]-4-(4-phenyl-4-hydroxypiperidino)butan-2-one |
| 10. | 4-(Piperidino) | 3-[4-(Piperidino)piperidinomethyl]-4-(4-piperidinopiperidino)-butan-2-one |
| | Unsaturated Product | 3-[4-(Piperidino)piperidinomethyl]-3-buten-2-one |
| 11. | 4-(Pyrrolidino) | 3-[4-(Pyrrolidino)piperidinomethyl]-4-(4-pyrrolidinopiperidino)-butan-2-one |
| | Unsaturated Product | 3-[4-(Pyrrolidino)piperidinomethyl]-3-buten-2-one |

Di-Hydrochloride of 3-[(4-Hydroxypiperidino)methyl]-4-(hydroxypiperidino)-butan-2-one The title ketone (2.84 g., 0.01 mole) is dissolved in 50 ml. of dry ether and reacted with dry hydrogen chloride until no further precipitation. The product after aging in the mother liquor is separated, washed with ether and dried at 40° C. under reduced pressure.

EXAMPLE 2

3-[(4-Hydroxypiperidino)methyl]-3-buten-2-one

3-[(4-Hydroxypiperidino)methyl]-4-(hydroxypiperidino)butan-2-one (1 g.) was dissolved in 8 ml. of ethyl alcohol and added to a cooled solution of oxalic acid anhydrous (0.9 g.) in 5 ml. of ethyl alcohol. After standing at 0° C. for five minutes, the resultant precipitate was filtered. The filtrate was stripped of solvent under reduced pressure and the residual oil taken up in a small volume of water, saturated with potassium carbonate and then extracted with ether. The ether solution was dried over anhydrous sodium sulphate, filtered and the filtrate stripped of ether. The residual oil, approx. 0.1 g., was characterized including a proton nuclear magnetic resonance spectrum in deuterated dimethylsulfoxide. There were two vinylic protons, at 5.9 and 6.1 ppm downfield from the reference tetramethylsilane.

Additional 3-[substituted piperidinomethyl]-3-buten-2-ones are prepared by this procedure and include

| Product | Unsaturated Product |
|---|---|
| 3-[(3-Hydroxypiperidino)methyl]-4-(3-hydroxypiperidino)butan-2-one | 3-[(3-Hydroxypiperidino)methyl]-3-buten-2-one |
| 3-[(3-Hydroxymethylpiperidino)methyl]-4-(3-hydroxymethylpiperidino)butan-2-one | 3-[(3-hydroxymethylpiperidino)methyl]-3-buten-2-one |
| 3-[(4-Carboxypiperidino)methyl]-4-(4-carboxypiperidino)butan-2-one | 3-[(4-Carboxypiperidino)methyl]-3-buten-2-one |
| 3-[(3-Carbamylpiperidino)methyl]-4-(3-carbamylpiperidino)-butan-2-one | 3-[(3-Carbamylpiperidino)methyl]-3-buten-2-one |
| 3-{[4-(N-methylcarbamyl)piperidino]methyl}-4-[4-(N-methylcarbamylpiperidino)]-butan-2-one | 3-[4-(N-Methylcarbamyl)piperidino]methyl-3-buten-2-one |
| 3-[(4-Ethoxycarbonylpiperidino)methyl]-4-(3-ethoxypiperidino)butan-2-one | 3-[(4-Ethoxycarbonylpiperidino)methyl]-3-buten-2-one |
| 3-[(4-Isopropylpiperidino)methyl]-4-(4-isopropylpiperidino)butan-2-one | 3-[(4-Isopropylpiperidino)methyl]-3-buten-2-one |
| 3-[(3-Methyl-4-hydroxymethylpiperidino)methyl]-4-(3-methyl-4-hydroxymethylpiperidino)butan-2-one | 3-[(3-Methyl-4-hydroxymethylpiperidino)methyl]-3-buten-2-one |
| 3-[(4-Phenyl-4-hydroxypiperidino)methyl]-4-(4-phenyl-4-hydroxypiperidino)-butan-2-one | 3-[(4-Phenyl-4-hydroxypiperidino)methyl]-3-buten-2-one |

Methiodide Quaternary Salt of 3-([(4-hydroxypiperidino) methyl]-3-buten-2-one

The olefinic basic ketone (1.83 g., 0.01 mole) is dissolved in 25 ml. of dry ether and mixed with 0.7 ml. of methyl iodide. After stirring overnight an additional 1 ml. of methyl iodide is added and an additional 12 hr. of reaction time is employed. The separated product is washed repeatedly with dry ether and dried.

Benzyl Bromide Quaternary Salt

The basic ketones (1.83 g., 0.01 mole) is dissolved in 15 ml. of acetone and mixed with benzyl bromide (1.9 g., 0.011 mole). The solution is heated in a bath at 70° C. for 12 hr. The solid product is separated, washed with acetone followed by ether and then dried at 45° C. under vacuum.

EXAMPLE 3

3-Diethylaminomethyl-4-(4-hydroxypiperidino)butan-2-one Step A. 1,1-Bis-(Diethylaminomethyl)acetone This compound was prepared in the manner described in J.A.C.S. 65, 972 (1943) by adding a solution of 210 ml. diethylamine in 400 ml. water to 300 ml. acetone, to which was then added without cooling 170 ml. 37% aqueous formaldehyde solution. The reaction evolved heat, and after standing 16 hours, the 2-phase reaction mixture was made alkaline by the addition of dilute sodium hydroxide, the water phase saturated with sodium chloride and the upper oil phase separated. The brine layer was extracted with three 400 ml. portions of ether; the ether extracts were combined and joined with the oil. The ether solution was dried over magnesium sulphate, and the solvent removed by distillation. The residual oil was fractionated by distillation under reduced pressure to yield the product, b.p. 103°–111°/6 mml.

The reaction was run similarly with the substitution of equimolar quantities of other organic bases in place of diethylamine, namely, dimethylamine, di-n-propylamine, di-isobutylamine, di-2-ethylhexylamine, di-allylamine, piperidine and pyrrolidine. The isolation of the oily reaction product was readily achieved by phase separation. Purification, if desired, could be achieved by fractional distillation or by fractional crystallization of the salts prepared in anhydrous alcohol or ether with inorganic acids. The free bases containing two nitrogen-bearing groups substituted on the one carbon atom of the acetone molecule were high boiling oils of very slight color showing low water solubility and being readily soluble in the common organic solvents. Water-saturated solutions showed pH values above 10.

Step B. 3-Diethylaminomethylbut-3-en-2-one

The intermediate olefinic ketone is prepared by the procedure of H.M.E. Cardwell [J. Chem. Soc., 1058 (1950)]. The ketone obtained from A., 22.8 g., in 25 ml. of ethanol was added to a solution of 25 g. of anhydrous oxalic acid in 75 ml. of ethanol. The mixture was cooled to 0° C., filtered to remove diethylamine hydrogen oxalate and the mother liquor evaporated to dryness under reduced pressure. The residue was dissolved in a little water, treated with potassium carbonate and extracted with ether. The ether was dried over anhydrous sodium sulphate and the residue distilled. After re-distillation the product was obtained as an oil, b.p. 82° C./18 mm. Similarly, the other 1,1-bis-(di-substituted aminomethyl)acetones obtained as in A. can be converted to the corresponding 3-disubstituted aminomethylbut-3-en-2-ones. The di-substituted amino term as previously indicated also comprises pyrrolidine and piperidine alicyclic ring analogs. For example, 3-(piperidinomethyl)but-3-en-2-one boils at 135°-139° C./15 mm. and is synthesized following the same procedure from 1,1-bis(-piperidinomethyl)acetone.

The following are synthesized using this procedure:

| Amine + | Unsaturated Product→ | Product |
| --- | --- | --- |
| Dimethylamine | 3-[(3-Hydroxypiperidino-methyl]-3-buten-2-one | 3-Dimethylamino-methyl-4-(3-hydroxypiperi-dino)butan-2-one |
| Di-n-octyl-amine | 3-[(3-Hydroxymethyl-piperidino)methyl]-3-buten-2-one | 3-Di-n-octyl-aminomethyl-4-(3-hydroxy-methylpiperi-dino)butan-2-one |
| Ethanol-amine | 3-[(4-carboxypiperidino)methyl]-3-buten-2-one | 3-[(4-carboxy-piperidino)-methyl]-4-(2-hydroxyethyl-amino)butan-2-one |
| Dicyclo-hexylamine | 3-[(3-carbamylpiperidino)-methyl]-3-buten-2-one | 3-[(3-carbamyl-piperidino)methyl]-4-dicyclohexyl-amino-butan-2-one |
| Pyrrolidine | 3-[(4-N-methylcarbamyl)-piperidino]methyl-3-buten-2-one | 3-[4-(N-methyl-carbamyl)piperi-dino]methyl-4-(pyrrolidino)-butan-2-one |
| Piperidine | 3-[(4-ethoxycarbonylpiperidino)methyl]-3-buten-2-one | 3-[(4-Ethoxy-carbonylpiperi-dino)methyl]-4-(piperidino)-butan-2-one |
| Diethanol-amine | 3-[(4-Isopropylpiperi-dino)methyl]-3-buten-2-one | 3-di-(2-hydroxy-ethyl)aminoethyl-4-(4-isopropyl-piperidino)butan--2-one |
| n-Hexylamine | 3-[(3-methyl-4-hydroxy-methylpiperidino)methyl]-3-buten-2-one | 3-n-Hexylamino-methyl-4-(3-methyl-4-hydroxy-methylpiperidino)-butan-2-one |
| Cyclopentyl-amine | 3-[(4-Phenyl-4-hydroxy-piperidino)methyl]-3-buten-2-one | 3-(Cyclopentyl-aminoethyl-4-(4-phenyl-4-hydroxypiperidino)-butan-2-one |

What is claimed is:

1. A compound of the formula:

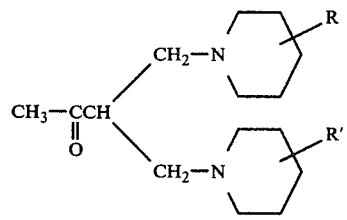

wherein R and R$^1$ are C$_1$ to C$_3$ alkyl, hydroxy, C$_1$ to C$_3$ hydroxyalkyl, phenyl, carboxy, carboxamido, N-loweralkylcarboxamido said alkyl having up to four carbon atoms, loweralkoxycarbonyl said alkoxy having up to four carbon atoms, 1-pyrrolidinyl and 1-piperidinyl, provided that R and R$^1$ are substituted at either the 3 or 4 position of the piperidine rings and further provided that said piperidine rings are identically substituted.

2. A compound according to claim 1 which is 3-[(4-hydroxypiperidino)methyl]-4-(4-hydroxypiperidino)-butan-2-one.

3. An antimicrobial composition comprising an antimicrobially effective amount of a compound of the formula:

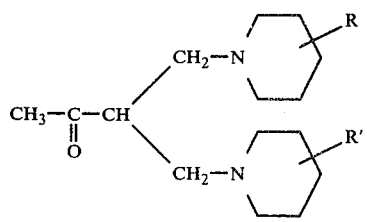

wherein R and R$^1$ are C$_1$ to C$_3$ alkyl, hydroxy, C$_1$ to C$_3$ hydroxyalkyl, phenyl, carboxy, carboxamido, N-loweralkylcarboxamido said alkyl having up to four carbon atoms, lower alkoxycarbonyl said alkoxy having up to four carbon atoms, 1-pyrrolidinyl and 1-piperidinyl, provided that R and R$^1$ are substituted at the 3 or 4 position of the piperidine rings and further provided that said piperidine rings are identically substituted.

4. A composition according to claim 3 where the carrier is selected from the group consisting of talc, corn starch, alumina and diatomaceous earth.

* * * * *